(12) United States Patent
Wu

(10) Patent No.: US 8,236,027 B2
(45) Date of Patent: *Aug. 7, 2012

(54) SURGICAL THREAD

(76) Inventor: Tze Liang Woffles Wu, Berjaya (SG)

( * ) Notice: Subject to any disclaimer, the term of this patent is extended or adjusted under 35 U.S.C. 154(b) by 31 days.

This patent is subject to a terminal disclaimer.

(21) Appl. No.: 11/123,214

(22) Filed: May 6, 2005

(65) Prior Publication Data

US 2005/0267532 A1    Dec. 1, 2005

Related U.S. Application Data

(63) Continuation of application No. PCT/SG2005/000104, filed on Mar. 31, 2005.

(30) Foreign Application Priority Data

Apr. 7, 2004  (WO) ................ PCT/SG2004/000090

(51) Int. Cl.
*A61B 17/04* (2006.01)
(52) U.S. Cl. ....................................... 606/228
(58) Field of Classification Search .................. 606/228, 606/204.35; 128/898
See application file for complete search history.

(56) References Cited

U.S. PATENT DOCUMENTS

| | | | |
|---|---|---|---|
| 3,123,077 A | 3/1964 | Alcamo | |
| 4,259,959 A | 4/1981 | Walker | |
| 4,467,805 A | 8/1984 | Fukuda | |
| 5,342,376 A | 8/1994 | Ruff | |
| 5,376,118 A * | 12/1994 | Kaplan et al. | ............... 623/23.72 |
| 5,584,859 A | 12/1996 | Brotz | |
| 5,931,855 A | 8/1999 | Buncke | |
| 6,241,747 B1 | 6/2001 | Ruff | |
| 6,270,517 B1 | 8/2001 | Brotz | |
| 6,599,310 B2 | 7/2003 | Leung et al. | |
| 6,773,450 B2 | 8/2004 | Leung et al. | |
| 6,848,152 B2 | 2/2005 | Genova et al. | |
| 2003/0074023 A1 * | 4/2003 | Kaplan et al. | ................ 606/228 |
| 2004/0060409 A1 | 4/2004 | Leung et al. | |
| 2004/0060410 A1 | 4/2004 | Leung et al. | |

(Continued)

FOREIGN PATENT DOCUMENTS

BE    1014364    9/2003

(Continued)

OTHER PUBLICATIONS

Bryd et al. "Achieving Aesthetic Balance in the Brow, Eyelids, and Midface"; Plast. Reconstr. Surg. 110 (3): 926-33, 2002).*
Yousif et al. "The Midface Sling: A new technique to rejuvenate the midface"; Plast. Reconstr. Surg. 110: 1541, 2002.*

(Continued)

*Primary Examiner* — Katherine Dowe
(74) *Attorney, Agent, or Firm* — Nixon Peabody LLP; Jeffrey L. Costellia

(57) ABSTRACT

A surgical thread for plastic surgery operations includes a clear section and multiple sharp projections on either side of the clear section. The clear section is devoid of projections while the projections on both sides of the clear section are inclined toward the clear section. There is also a method of performing plastic surgery operations using this surgical thread which includes threading the thread subcutaneously through tissue and/or muscle and in a manner such that the thread is folded back on itself as a loop or sling. The thread tension is then adjusted from both ends of the thread which extend out of two separate exit points to achieve a desired lift. The projections resist thread pull in the direction of the entry point and the clear section is located at the fold.

41 Claims, 8 Drawing Sheets

U.S. PATENT DOCUMENTS

| | | | |
|---|---|---|---|
| 2004/0088003 A1* | 5/2004 | Leung et al. | 606/228 |
| 2004/0162580 A1* | 8/2004 | Hain | 606/229 |
| 2004/0226427 A1 | 11/2004 | Trull et al. | |
| 2004/0267315 A1* | 12/2004 | Wolf et al. | 606/230 |

FOREIGN PATENT DOCUMENTS

| | | | |
|---|---|---|---|
| BE | 1014364 A6 | | 9/2003 |
| CA | 2 487 263 A1 | | 12/2003 |
| EP | 1075843 | | 2/2001 |
| GB | 1091282 | * | 11/1967 |
| GB | 1 508 627 | | 4/1978 |
| WO | WO 96/06565 | | 3/1996 |
| WO | WO 98/52473 | | 11/1998 |
| WO | WO 00/51658 | | 9/2000 |
| WO | WO 2004/030705 A2 | | 4/2004 |

OTHER PUBLICATIONS

Wu, "Barbed Sutures in Facial Rejuvenation", Aesthetic Surgery Journal—Nov./Dec. 2004, vol. 24, No. 6, pp. 1-7.

Sulamanidze, M.D. et al., "Facial Lifting with "APTOS" Threads"; www.fonendo.com; Jul. 18, 2001.

PCT International Search Report for Application No. PCT/SG2004/000090 dated May 25, 2004.

U.S. Appl. No. 10/85,480, filed Apr. 7, 2004 to Wu.

Woffles T.L. Wu, *Aesthetic Surgery of the Facial Mosaic*, the chapter titled "Innovative Uses of BOTOX and the WOFFLES Lift", ed D Panfilov. Pub. Springer, Berlin Heidelberg (2006):636-649.

"Barbed Sutures in Facial Rejuvenation" published in the Aesthetic Surgery Journal Nov./Dec. 2004 issue.

* cited by examiner

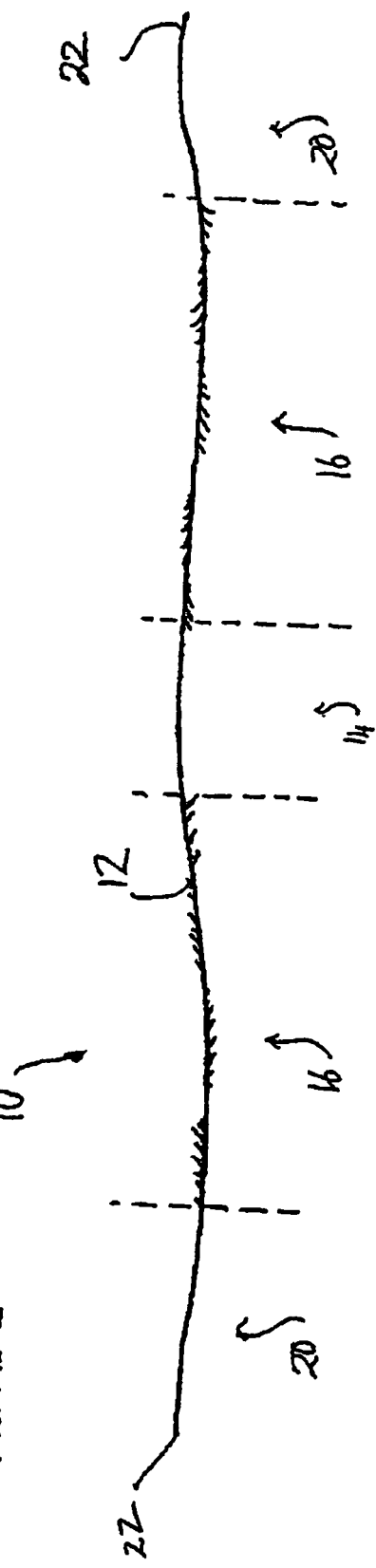
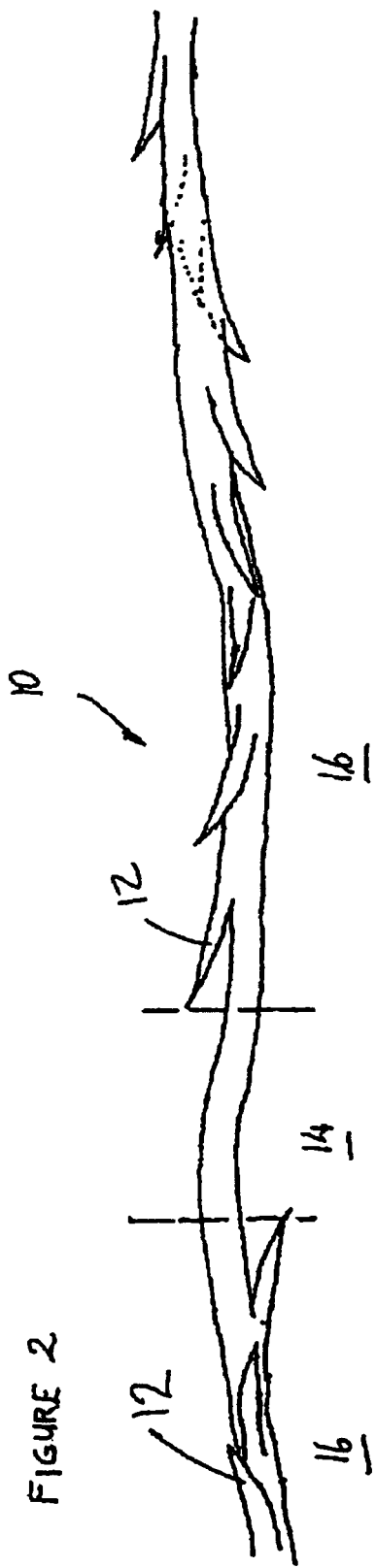
FIGURE 1
FIGURE 2

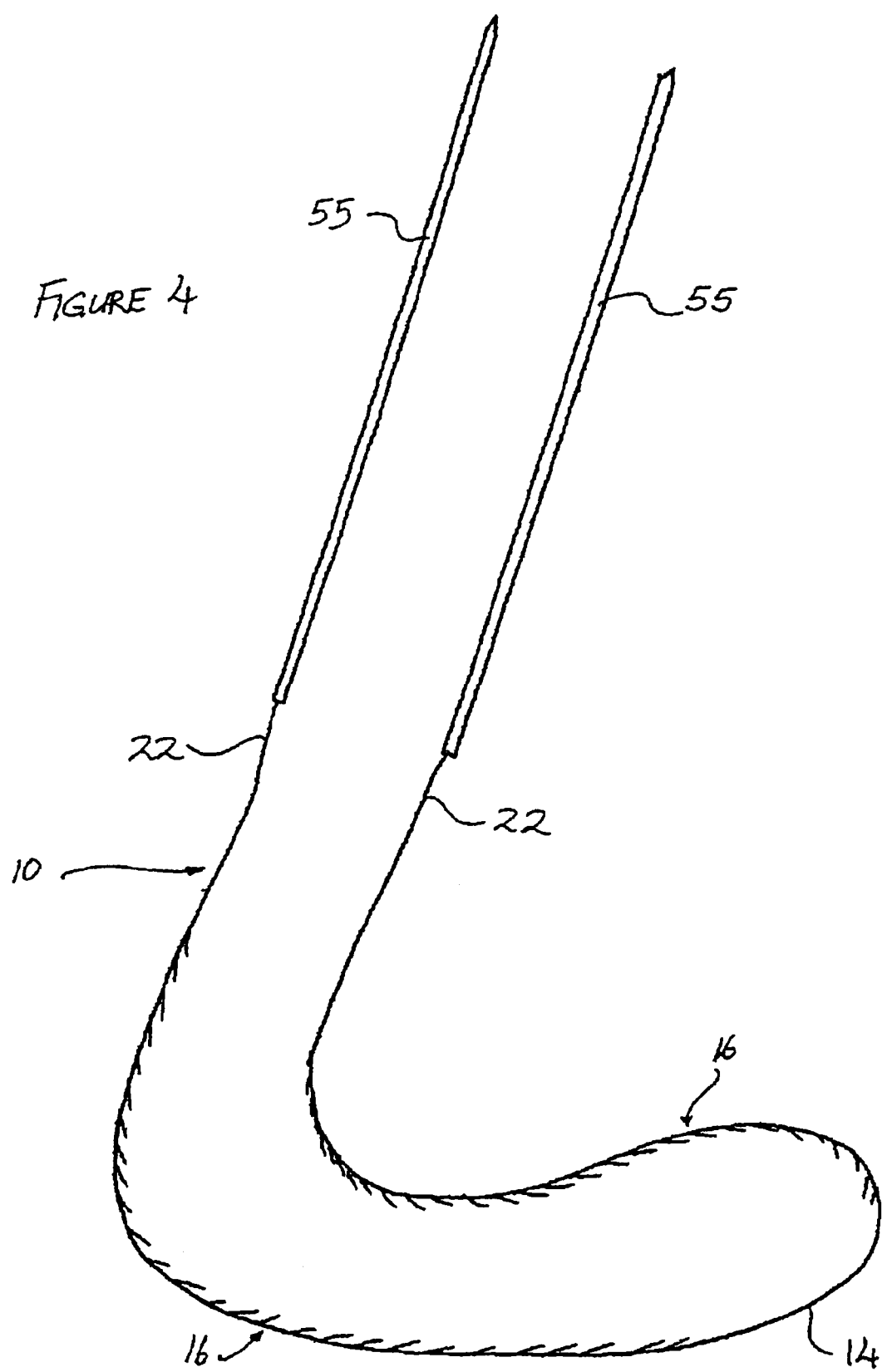

SURGICAL THREAD

The present invention relates generally to a surgical thread for use in plastic surgery operations and a method of performing plastic surgery operations using the surgical thread.

BACKGROUND OF THE INVENTION

Traditional face lifting techniques involve extensive dissection of the different layers of facial tissue and skin. These tissues are then redraped and rearranged in an upward and posterior direction.

This face lift technique inevitably results in long scars and the risk of complications including skin necrosis, nerve damage, vascular damage, hair loss, displacement of the ears and an unnatural attitude of the face. The largest drawback of these surgical techniques is the significant swelling and bruising caused with downtime from recovery lasting between 2 to 6 weeks, in which time patients are unable to work and prefer to avoid social situations.

Various techniques have been developed over the years to minimise the scarring and tissue dissection caused by face lift procedures. One known technique uses a barbed suture where the barbs are oriented in a direction opposite the thread tension. This suture is inserted as a gentle curve under soft tissue conferring a modest lift as well as a bunching up of the soft tissue, which is desirable in the malar or cheek area.

While this technique has eliminated the need for dissecting and lifting facial tissue and eliminated the scarring and consequential complications, it fails to be as effective in lifting heavy facial soft tissues such as that in the forehead and brow, mid face, jowls, lateral face and neck. Heavier tissue in these areas impart a significant pull against the barbs on the surgical thread leading to early slackening and dropping of the facial tissue. Additionally, the "bunching up" effect is not as desirable in the areas of the forehead, jowls, neck and lateral face where tissue is expected to be smooth and taut for a youthful look.

There is thus a need for an improved surgical thread and procedure that is minimally invasive and will effectively suspend tissue.

SUMMARY OF THE INVENTION

In one aspect, a surgical thread for plastic surgery operations comprising a clear section and multiple sharp projections on either side of the clear section, wherein the clear section is devoid of projections, and the projections on both sides of the clear section are inclined toward the clear section.

In another aspect, a method of performing plastic surgery operations using a surgical thread having a clear section and multiple sharp projections on either side of the clear section, wherein the clear section is devoid of projections, and the projections on both sides of the clear section are inclined toward the clear section, the method including:

making an incision into tissue at an entry point defining the point of tissue lift;

inserting a cannula in a first pass subcutaneously between the entry point and a first exit point from where tissue is to be suspended;

threading one end of the surgical thread from the entry point through the cannula and out of the first exit point until the clear section nears or enters the incision;

removing the cannula and reinserting the cannula in a second pass between the entry point and a second exit point spaced from the first exit point;

threading the other end of the surgical thread through the cannula and out of the second exit point thereby folding the thread back on itself;

removing the cannula and adjusting the thread tension from both ends of the thread to achieve a desired lift, the projections resisting thread pull in the direction of the entry point and the clear section being located at the fold;

cutting the thread ends; and closing the incision at the entry point.

In yet another aspect, a method of performing plastic surgery operations using a surgical thread having a clear section and multiple sharp projections on either side of the clear section, wherein the clear section is devoid of projections, and the projections on both sides of the clear section are inclined toward the clear section, the method including:

making an incision into tissue at an entry point defining the point of tissue lift;

threading one end of the surgical thread from the entry point subcutaneously through tissue and/or muscle and out of a first exit point from where tissue is to be suspended, whereby the thread is threaded until the clear section nears or enters the incision;

threading the other end of the surgical thread through the entry point and subcutaneously through tissue and/or muscle and out of a second exit point spaced from a first exit point thereby folding the thread back on itself;

adjusting the thread tension from both ends of the thread to achieve a desired lift, the projections resisting thread pull in the direction of the entry point and the clear section being located at the fold; and cutting the thread ends and closing the incision at the entry point.

BRIEF DESCRIPTION OF THE DRAWINGS

The present invention is described further by way of example with reference to the accompanying drawings of which:

FIG. 1 is a side view of a surgical thread according to an embodiment of the present invention;

FIG. 2 is an enlarged view of a section of the surgical thread in one embodiment of the invention;

FIG. 4 illustrates a second embodiment of the surgical thread;

DETAILED DESCRIPTION OF PREFERRED EMBODIMENTS

Figure 3A:
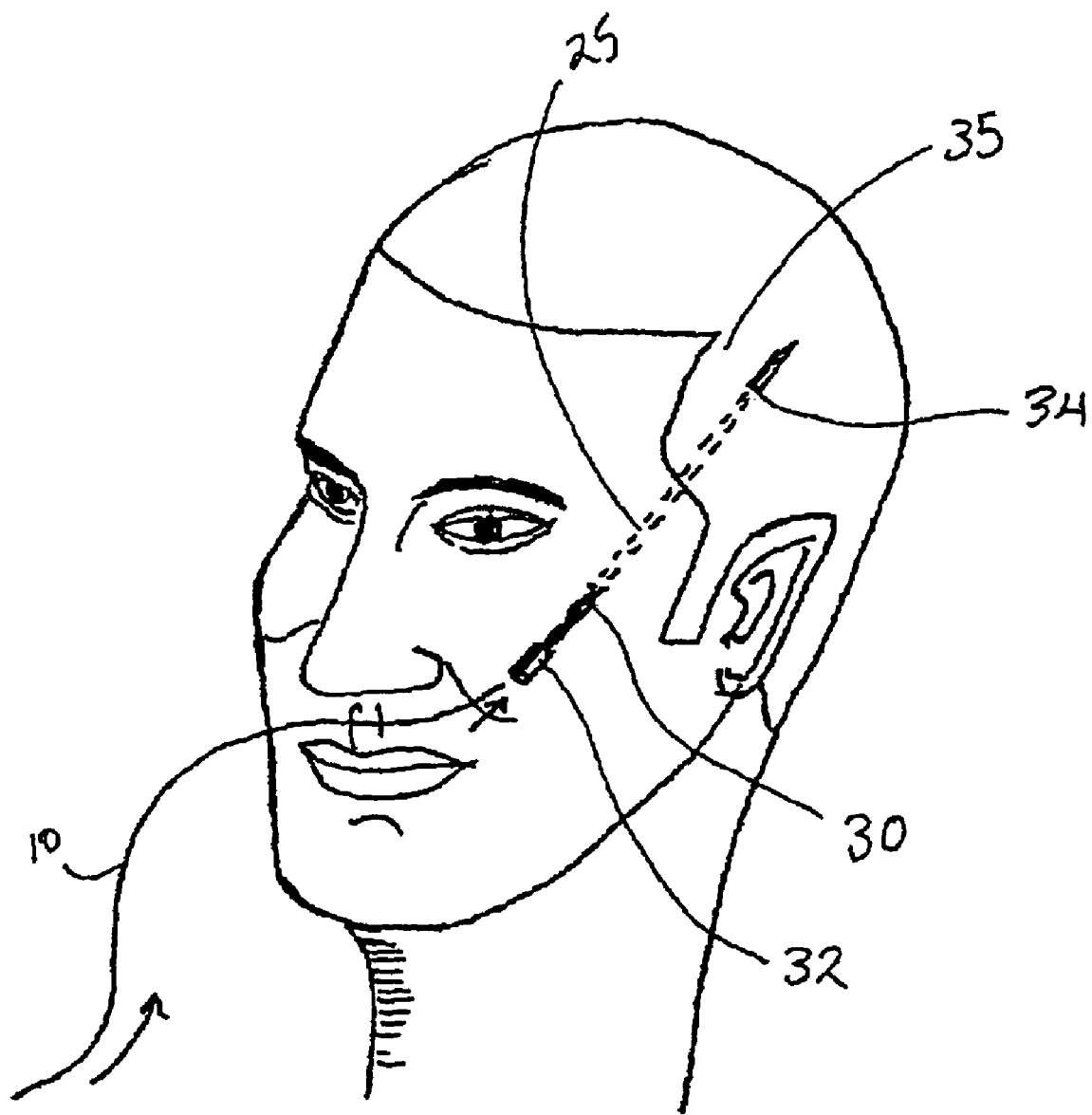
FIG. 3A illustrates a first step in a face lift procedure according to an embodiment of the present invention.

The drawings illustrate surgical threads and methods of performing operations with the surgical thread which produce an improved soft tissue lift capable of sustaining a longer lift than that achievable with known surgical threads and face lift procedures.

In the following description specific examples are made to surgical lifting operations on a person's face. However, it is to be understood that the procedure finds equal applicability, and is likely to be used in, other procedures including breast lifting, buttock lifting and the lifting of any other part of the human body that may be desired to be lifted.

While the description herein refers specifically to surgical procedures performed on humans, it is conceivable that the procedure could be performed on non-humans, and specifically in veterinary medicine on animals.

FIG. 1 illustrates a length of surgical thread 10 for use in surgical procedures, and in particular plastic and cosmetic surgery. The thread 10 can be made of any soft, resilient and bio-compatible material. In a preferred embodiment the thread material is made of polypropylene but it is also envisaged that other suitable materials could include gold, stainless steel and dissolvable suture materials such as polydiaxonone. Additionally, the thread may be made of varying grades and thicknesses of these materials, depending on the area being lifted and on the desired effect. In this embodiment the thread thickness is between a 3.0 gauge (0.3 mm diameter) and a 2.0 gauge (0.35 mm diameter) suture.

The surface of the thread 10 contains a number of spaced bi-directional sharp projections known as barbs 12. The surgical thread 10 is divided into sections or zones and barbs 12 occupy two of these zones. Specifically, a clear zone or section 14 is located substantially at the mid center of the length of thread and is devoid of any barbs 12. The surface of the surgical thread 10 in the clear zone 14 is relatively smooth.

On either side of the clear zone 14 are barb sections 16 where the surface of the thread is provided with barbs 12. The barbs 12 are inclined relative to the thread such that when inserted into soft tissues the barbs allow the thread to be pulled with ease through the tissue in one direction but resist pulling, or unthreading, of the thread in the opposite direction by digging their sharp ends into the surrounding soft tissue in resistance.

The inclination of the barbs in the two barb sections 16 on either side of the clear zone 14 are oriented in opposite directions. FIG. 2 shows in an enlarged view the clear zone 14 and barb zones 16 on either side of the clear zone. It can be seen from this figure that the barbs 12 to the left of the clear zone 14 are inclined towards the right hand side of the figure, whereas the barbs 12 to the right of the clear zone 14 are inclined in the opposite direction to the left hand side of the figure. The barbs in both barb zones are all pointing towards the clear zone 14.

The barbs are created by cutting or etching into the surface of the surgical thread 10 in a manner to produce a sharp tip 18 of the barb 12.

The barbs are furthermore spaced around the surgical thread in a spiral formation. This can be seen in FIG. 2. The spiral nature of the barbs means that when the surgical thread is threaded subcutaneously through soft tissue the thread is able to achieve a better hold on the surrounding tissue in all directions.

End zones 20 are located at the ends of the surgical thread and next to barb zones 16. End zones 20 are also devoid of barbs 12.

In a preferred embodiment the surgical thread is 60 to 65 cm long. This includes the clear zone 14 being about 4 cm in length, two barbed zones 16 each about 20 cm in length and two end zones 20 each 8 to 10.5 cm in length.

The barbs are spaced at intervals of about 1 to 2 mm. One 360° spiral revolution spans about approximately 35 to 45 mm. Approximately 18 to 22 barbs are contained in one spiral revolution. Therefore, a barbed zoned 20 cm in length contains about 5 spirals.

Each barb is 1 to 2 mm long and occupies ⅙ to ¼ the thickness of the thread.

The above dimensions are illustrative of a working embodiment of the surgical thread but are not to be considered in a restrictive manner. For example, the length of the surgical thread may vary from short to long depending on the area and amount of soft tissue to be lifted. In other words, a short lift (e.g. eyebrow lift) would require a shorter surgical thread than a longer lift (e.g. chin lift).

Variations to the above preferred dimensions while retaining the concept of the surgical thread are possible. For example, the barb revolutions may be quite tight with only 4 to 6 barbs per revolution. Alternatively, the spacing between barbs may vary, or the barb lengths themselves may be shorter or longer, depending on the precise end use of the thread and limitations of the manufacturing equipment.

The present surgical thread 10 is used in a manner to create a "sling" effect on the tissue portion to be lifted by the surgery. In other words, the thread is intended to be doubled back on itself with the clear zone 14 defining the fold and engaging the portion of tissue to be lifted. Accordingly, rather than the tissue being lifted at a single point defined by the end of the threads, as currently known, the present thread lifts, or takes hold of, more tissue by using the sling created by the looped fold to lift the tissue, resulting in a more secure and reliable lift.

Meanwhile, the lift is anchored at end zones 20 (or in barb zones 16 if the thread is cut short) which are held at a higher gravitational point in tissue or muscle. End zones 20 are not, however, burdened with bearing the entire load of the lift. Owing to the distribution of inclined barbs along the embedded length of the surgical thread 10 the load is evenly borne against gravity along the thread length in a self retaining manner.

Figure 3B:
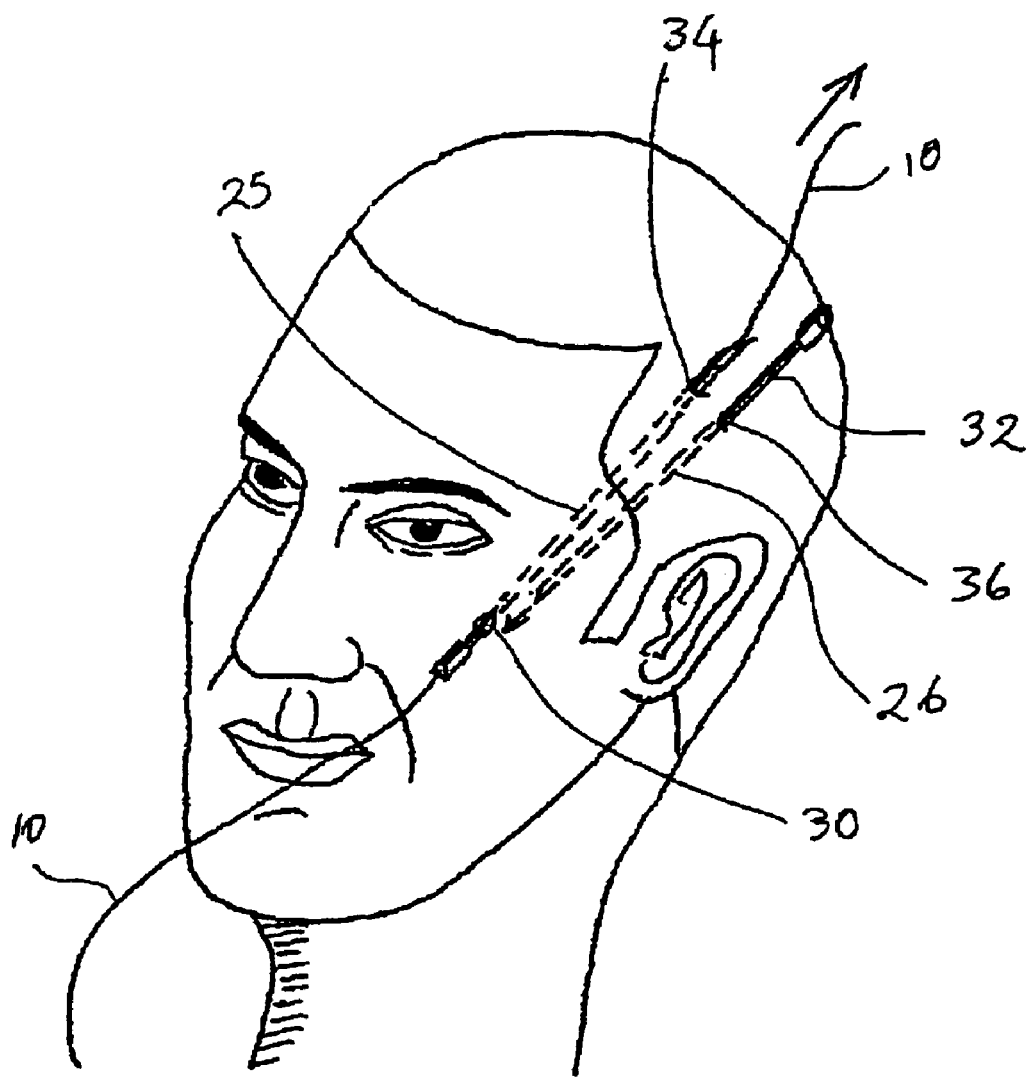
FIG. 3B illustrates a second step in the surgical procedure.
Figure 3C:
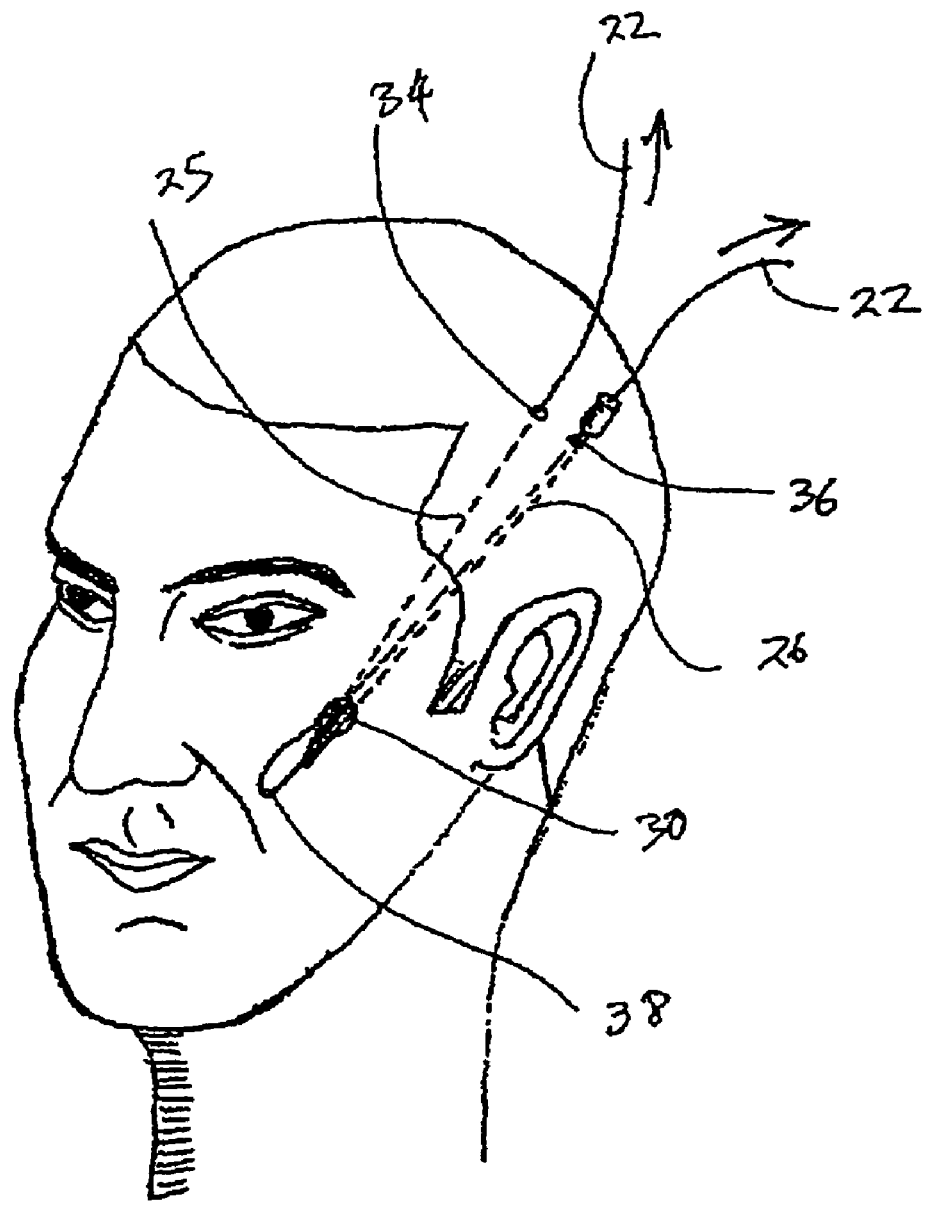
FIG. 3C illustrates a third step in the surgical procedure.

To illustrate more clearly the manner in which the thread is used in one embodiment, the steps in performing a surgical lift procedure are illustrated in FIGS. 3A to 3C. These figures illustrate a surgical technique in conducting a mid face suspension, or brow lift, on a person's face.

To begin, a surgeon first assesses the degree of slack in the pre-operational face and decides on the desired shape of the cheek or mid face area. The surgeon then marks the patient's skin identifying the point that will be lifted and the position of the two anchor points higher up the face from where the lift will be supported.

After administering to the patient local anesthetic blocks and local infiltration, the surgeon makes a small stab incision in the soft tissue at the lift point defining the entry point 30 as illustrated in FIG. 3A. Bluntly dissecting the stab incision the surgeon creates a space at the entry point 30 subcutaneously of about 0.5 cm radially around the stab incision. By creating this space dimpling in the post operative period is avoided.

A cannula 32, or insertion needle, is next introduced into the entry point 30 and threaded in a first pass 25 through the soft tissue and/or muscle under the skin following the markings on the skin and passing upwards along a glide plane to exit at a first exit point 34 at the scalp 35 behind the hairline, and namely on the hair bearing scalp.

As illustrated in FIG. 3A, one end of the surgical thread 10 is passed from the entry point 30 through the cannula 32 and up through the first exit point 34. The surgical thread is threaded through the cannula until the clear zone 14 nears or begins to enter the cannula at the incision entry point 30. The threading of the thread stops at this point, so that typically half the length of surgical thread is threaded and half remains hanging from the cannula at the entry point. Accordingly, at this stage the mid point of the thread is usually located around the entry point 30.

The cannula is then removed and compression is applied to the bleeding points.

FIG. 3B illustrates the next step and shows the second pass 26 of the cannula which begins at a second exit point 36 in the scalp behind the hair line a short distance from the first exit point 34. The second exit point is about 0.5 to 1 cm away from the first exit point. The cannula is then inserted down from the second exit point 36 through subcutaneous muscle and soft tissue to emerge through the initial stab incision at entry point 30. The path of this second path of the cannula is substantially parallel to the first path.

With the cannula forming a clear path through the facial tissue the other unthreaded end of the surgical thread 10 is threaded from entry point 30 up through the cannula to exit out of the second exit point 36. This step is illustrated by FIG. 3C.

The cannula is then removed and compression is applied to the bleeding points.

The surgical thread thus extends from the scalp 35 down through to the initial entry point 30 where the tissue is to be lifted, looped (or folded) back on itself to extend back up through the soft tissue and muscle below the skin to exit back at the scalp 35.

Loop 38 of the surgical thread 10 in FIG. 3C is at this point still located above the surface of the face. If threaded correctly, the loop 38 is formed by the clear zone 14 of the surgical thread 10. Additionally, the embedded sections of thread should include the barbed zones 16 in which the barbs are pointed downward toward the clear zone and hence towards the point of lift.

Tension is then applied to the thread by pulling up ends 22 at the exit points 34,36 in the directions illustrated by the arrows in FIG. 3C. Because the barbs point away from thread ends 22, the threads are able to be easily pulled and loop 38 is drawn through the entry point 30 incision grabbing hold of the tissue thereunder. Thread ends 22 are carefully adjusted to ensure that clear zone 14 is positioned substantially central of loop 38. The barbs on the embedded thread prevent the surgical threads slipping down or being pulled down under the natural gravitational tension in the tissue.

Once loop 38 has been drawn into the space created subcutaneously under entry point 30, further tension is applied on thread ends 22 until the desired level of mid face lift is achieved.

A needle (not shown) is then passed subcutaneously through the first and second exit points 34,36 on scalp 35 and one end of the surgical thread 10 is passed through the needle such that both ends now exit from the same exit point.

The tension on the thread is then readjusted and then secured at a final position with about three to four knots. The thread is then cut flush to the knot and urged under the skin. The tissue openings at the entry point 30 is then closed over by regular means such as stitching or compression.

In an alternative embodiment the thread ends can be simply left protruding from their respective exit points and cut flush with the exit opening. In this embodiment the thread relies on the angled barbs to retain it under the skin without slipping and to ensure stable elevation of the tissue.

If during the operation it is anticipated that a post operative adjustment will be required, the surgical thread 10 should only be knotted once and fair length of thread ends retained to enable subsequent tensioning and knotting of the thread.

The mid face lift procedure would then be repeated on the opposite side of the face at a suspension point symmetrical to the first point lifted.

The surgical procedure described above incorporates subcutaneous insertion of a cannula through which the surgical thread can be threaded. However, it is envisaged that other instruments may be used to pass the thread between the entry and the two exit points. A cannula is a suitable instrument to achieve this but other suitable instruments, such as a solid needle-type instrument, or the like, may also be used.

FIG. 4 illustrates a second embodiment of the surgical thread 10 which comprises the surgical thread described above but having solid tapered needles 55 attached to both ends of the thread 10. The tapered needles replace the need for using a cannula to pass the surgical thread 10 subcutaneously through the soft tissue and/or muscle. Instead, the needle is introduced into entry point 30 and threaded subcutaneously to the first exit point 34. Replacing the use of a hollow cannula with needles allows the thread to be inserted quickly and more directly through the soft tissue/muscle.

In threading needle 55 the surgical thread 10, which is attached to the needle, follows the needle through the soft tissue and out through the first exit point 34. The needle 55 at the other end of the thread is then inserted through entry point 30 and threaded subcutaneously through to the second exit point 36, which is spaced from the first exit point 34. Needle 55 is pulled through the second exit point 36 which in turn pulls that end of the surgical thread 10 through the second exit point. At this stage both needles have passed through one or the other exit point 34, 36 and the clear zone 14 forms a loop 38 at entry point 30. This is illustrated in FIG. 5.

Figure 5:
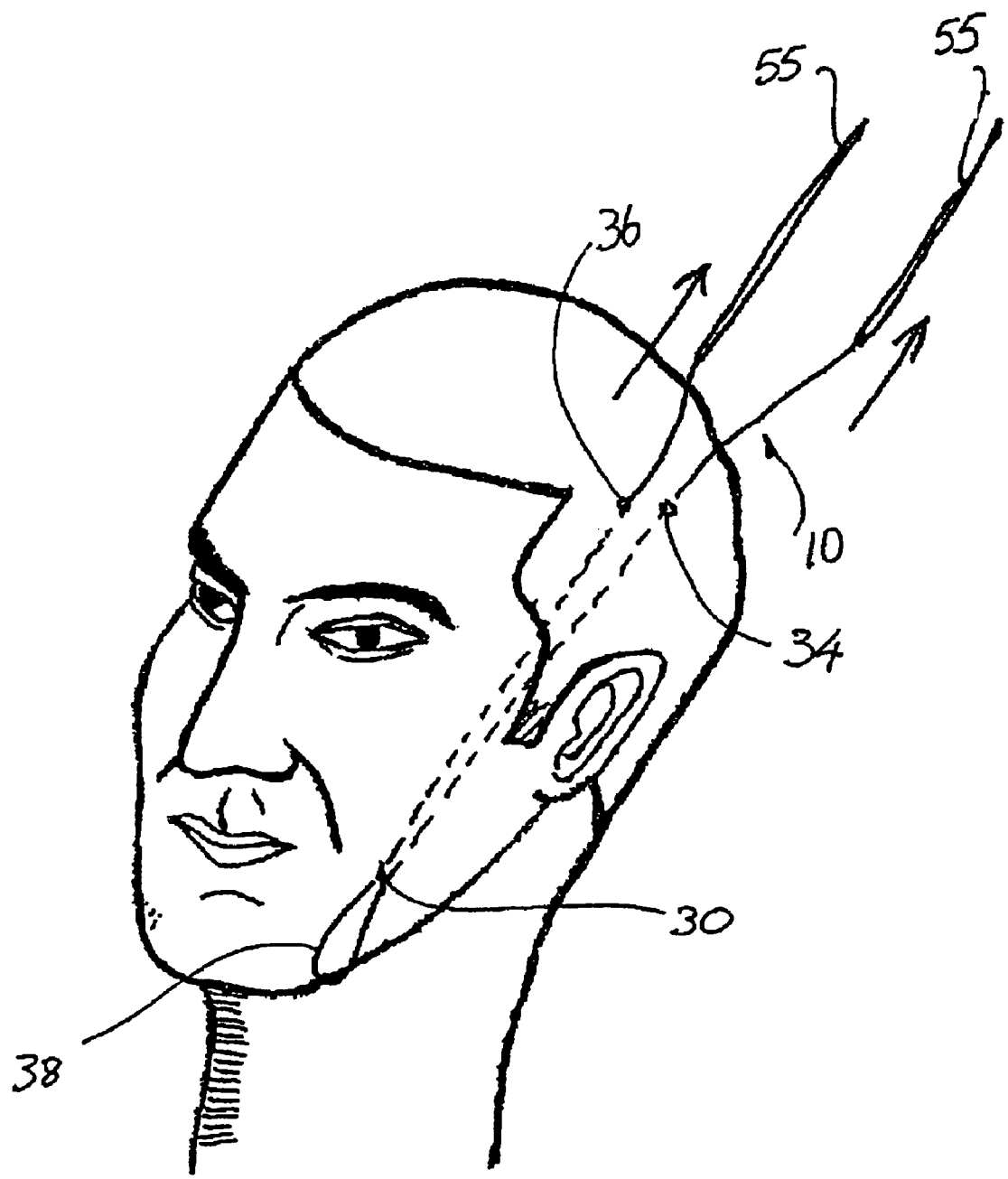
FIG. 5 illustrates the surgical thread of FIG. 4 threaded through a person's face.

The needles illustrated in FIGS. 4 and 5 are straight and long tapered solid needles. For a shorter lift, for example a hair line lift, the needles may be shorter. Some lift applications may require a curved needle in which case the needles at the end of the thread may be long or short curved needles. The needles themselves may be made of steel or any other suitable material.

In this second embodiment the surgical thread still creates a sling wherein the barbed portions of the thread are embedded in the soft tissue and the clear zone sits snuggly on a tissue bridge at the entry point. As described with the first embodiment, the ends of the surgical thread are pulled upwards to produce a tension in which the barbs engage the soft tissues to elevate the tissue. The threads are then cut flush to the scalp or, alternatively, the needles can be cut off from the threads and the thread ends knotted subcutaneously. Alternatively still, one needle may be threaded back into its corresponding exit point and threaded to the other exit point such that both thread ends emerge from the same exit point. Here, the threads are cut and knotted.

In one embodiment the ends of the surgical thread are attached to the long needles at manufacture. Alternatively, the needles may have eyes through which the thread ends may be threaded.

Figure 6:
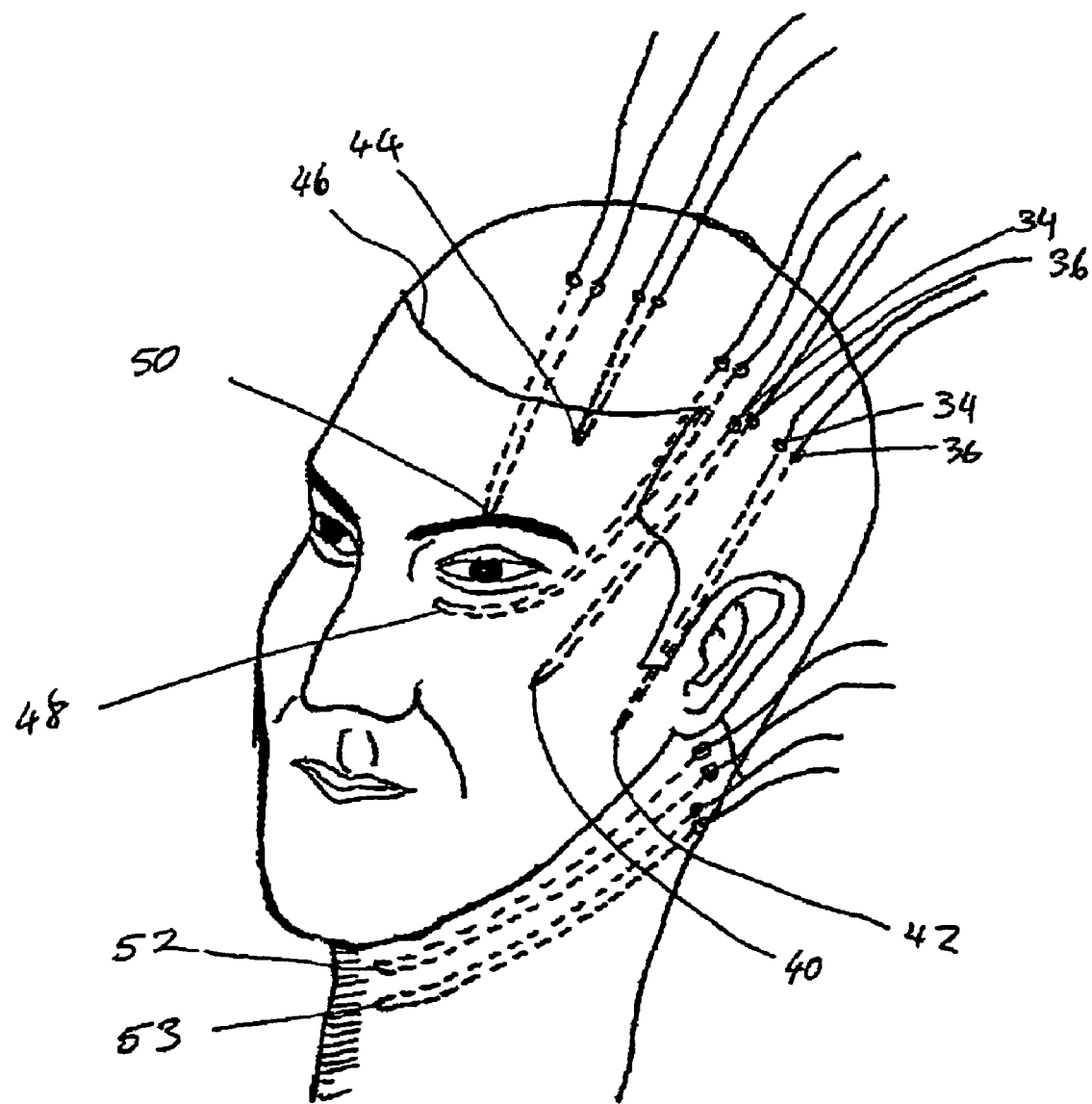
FIG. 6 illustrates various locations of performing a surgical procedure on a person's face according to an embodiment of the invention.

Other face lift procedures are performed in a similar manner using either the method of a cannula or using thread attached with needles. For example, another kind of mid face malar mound suspension may require lift of two points on each malar mound. These points are illustrated in FIG. 6 as first point 40 which is just below mid point of the malar mound and a second point 42 at the bottom of the malar mound, where a natural dimple occurs. In this procedure all four threads exiting two pairs of first and second exit points 34, 36 would need to be adjusted simultaneously to acquire the desired mid face lift.

An example of an intra hair line lift is illustrated in FIG. 6 with the lift occurring at point 44 on the hair line 46. A shorter length of surgical thread 10 would be required for this procedure. In practice, the normal thread length would be used and cut back to the appropriate length.

While all these operations may be performed with a standard length of surgical thread, the thread may be manufactured at different lengths to serve different lifting purposes for different areas of the anatomy. Similarly, the clear zone 14 may not necessarily be central to the length of thread but may be more to one side depending on the purpose for which the thread is used.

FIG. 6 also illustrates an eye lift 48, a brow lift 50 and a neck lift where the incisions for suspension are made at the platysmal bands 52 and 53. In this case the incision would be specifically made in the midline just medial to each band at the level of the mentocervical angle.

A technique for performing a jowl suspension is not illustrated but such a procedure would commence with making two stab incisions at the level of the angle of mandible through the bulk of the jowl mound and a third stab may be required at the level of the marionette line.

In all of the above examples, the surgical thread would be threaded in a similar fashion to that explained in relation to FIGS. 3A to 3C or FIGS. 4 and 5. In a similar manner, any tissue suspensions not involving the face, such as breast and buttocks, would involve the careful assessment of optimal thread entry and exit points followed by insertion of the cannula and threading the surgical thread in a sling as described above.

Figure 7A:
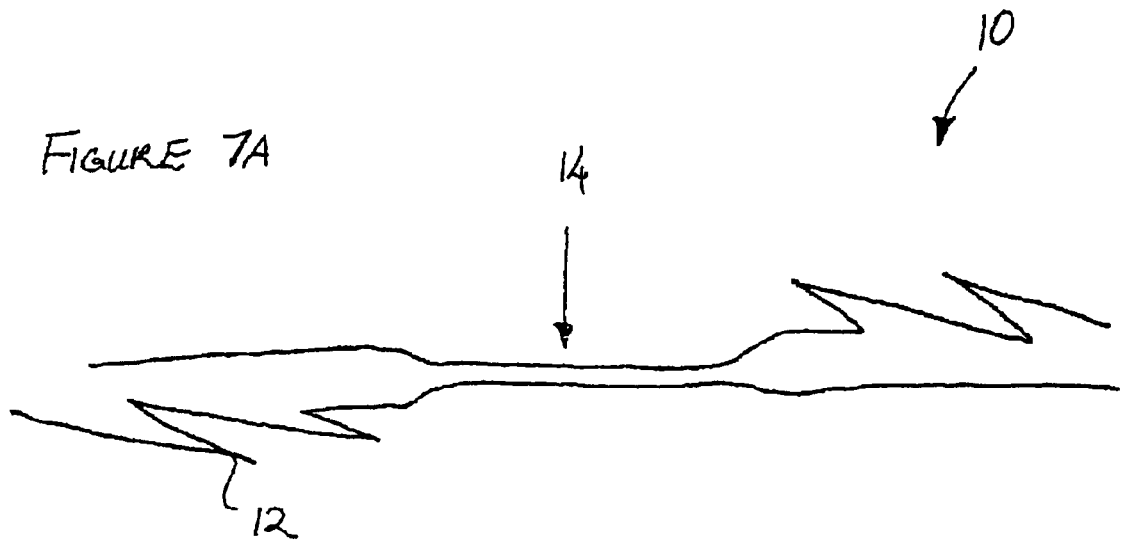
FIG. 7A is an enlarged view of a section of the surgical thread in another embodiment of the invention.
Figure 7B:
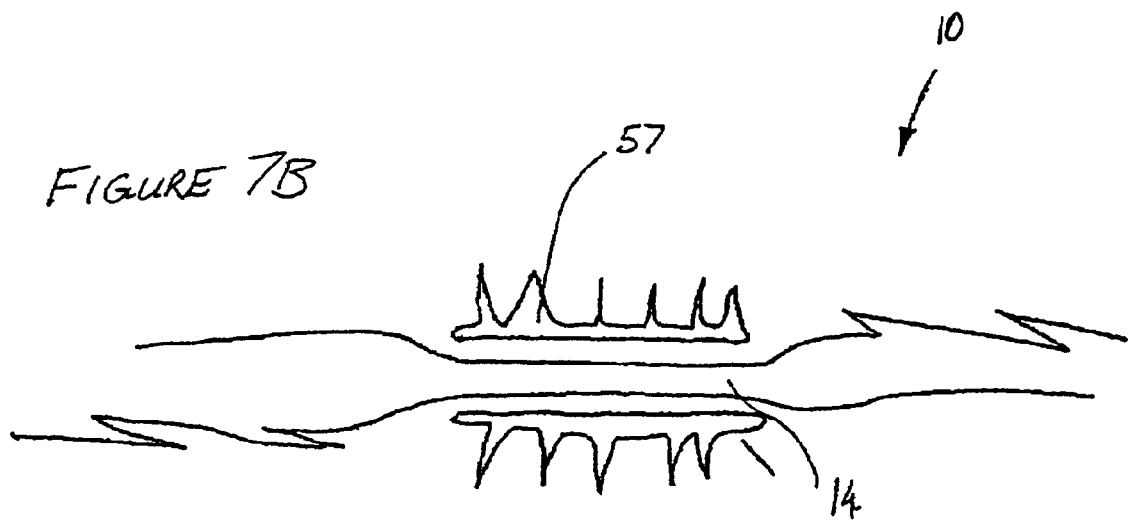
FIG. 7B is an enlarged view of a section of the surgical thread in yet another embodiment of the invention.

In another embodiment the central clear zone 14 may be modified to increase the "purchase" on the soft tissue, that is, the hold of the loop 38 on the soft tissue. Surgical threads have a tendency to sometimes cut through tissue when applied with force in a transverse direction of the thread. FIGS. 7A and 7B illustrate two modifications to the clear zone 14 that would prevent this cutting effect and increase the thread's hold on the tissue.

The clear zone 14 in FIG. 7A is flattened giving it a ribbon-like appearance wherein the flattened portion can more securely hold the tissue bridge at the entry point in a tissue lift. FIG. 7B illustrates a sheath or sleeve 57 surrounding clear zone 14. The sleeve may be provided with a roughened, corrugated or "furry" surface that increases the effective thickness of the clear zone 14 and causes the sleeve 57 to grab hold and adhere to the tissue more securely. In one embodiment the sleeve 57 may be made of a silastic or a dissolvable biodegradable material such as polylactic acid or polydiaxonone, or other suitable material.

In a third variation that is not illustrated the clear zone 14 may be braided with more than one thread to increase the effective thickness of the clear zone and reduce the sharp cutting effect through tissue that occurs with a single thread.

With the present "sling"-technique a stronger lift of tissue and muscle may be achieved and in fact the lift is doubled in strength because two lengths of thread are used to lift the tissue. The bi-directional spiral barbs prevent the tissue sagging and the thread slipping into early slackening. The clear zone of the thread allows room for adjusting and manipulating the thread once inserted subcutaneously and to provide strength and reliability to the 'sling' portion of the thread holding the lift.

The present surgical thread and method can be used for lifting more than just full, soft tissue but will also pull skin taut along the length of the thread to give the appearance of evenly smooth and taut skin. The overall result is a non-invasive procedure and a non-obvious, smooth face lift that will reliably last for years.

It will be understood to persons skilled in the art of the invention that many modifications may be made without departing from the spirit and scope of the invention.

The claims defining the invention are as follows:

1. A surgical thread for plastic surgery operations comprising a clear section and multiple sharp projections on either side of the clear section, wherein the clear section is devoid of projections and is approximately 4 cm in length to create a holding zone when the surgical thread is folded to form a loop or a sling at the clear section, and the projections on both sides of the clear section are inclined toward the clear section, wherein the surgical thread is approximately 60 to 65 cm long and has a diameter of approximately 0.30 to 0.35 mm, and wherein the sharp projections occupy a length of approximately 20 cm on either side of the clear section, and the surgical thread having end zones that are approximately 8 to 10.5 cm in length.

2. The surgical thread claimed in claim 1, wherein the end zones at the end of the surgical thread are clear of sharp projections.

3. The surgical thread claimed in claim 1, wherein the sharp projections are barbs cut into or etched into the thread.

4. The surgical thread claimed in claim 1, wherein the sharp projections are arranged in a spiral around the surgical thread such that one spiral revolution of sharp projections contains approximately 18 to 22 sharp projections.

5. The surgical thread claimed in claim 4, wherein one spiral revolution of sharp projections spans approximately 35 to 45 mm.

6. The surgical thread claimed in claim 1, wherein the sharp projections are spaced at intervals of about 1 to 2 mm.

7. The surgical thread claimed in claim 1, wherein each sharp projection is 1 to 2 mm in length.

8. The surgical thread claimed in claim 1, wherein each sharp projection occupies ⅙ to ¼ the thickness of the thread.

9. The surgical thread claimed in claim 1, wherein the thread is made of polypropylene.

10. The surgical thread claimed in claim 1, wherein the thread has two ends that are each attached to a needle.

11. The surgical thread claimed in claim 10, wherein the needles are short or long.

12. The surgical thread claimed in claim 10, wherein the needles are straight or curved.

13. The surgical thread claimed in claim 10, wherein the needles are made of steel.

14. The surgical thread claimed in claim 1, wherein the clear section is provided with a sleeve having a rough surface.

15. The surgical thread claimed in claim 14, wherein the sleeve is made of a silastic material or a dissolvable biodegradable material.

16. The surgical thread claimed in claim 15, wherein the dissolvable biodegradable material is a polylactic acid or polydiaxonone material.

17. The surgical thread claimed in claim 1, wherein the clear section is braided with more than one thread.

18. The surgical thread claimed in claim 1, wherein at least one end zone is attached to a needle.

19. A method of performing plastic surgery operations using a surgical thread having a clear section and multiple sharp projections on either side of the clear section, wherein the clear section is devoid of projections, and the projections on both sides of the clear section are inclined toward the clear section, the method including:

making an incision into tissue at an entry point defining the point of tissue lift;

threading one end of the surgical thread from the entry point subcutaneously through tissue and/or muscle and out of a first exit point from where tissue is to be suspended, whereby the thread is threaded until the clear section nears or enters the incision;

threading the other end of the surgical thread through the entry point and subcutaneously through tissue and/or muscle and out of a second exit point spaced from a first exit point thereby folding the thread back on itself to form a loop or sling;

adjusting the thread tension from both ends of the thread to achieve a desired lift along a direction from the point of tissue lift toward the first and second exit points, the projections resisting thread pull in the direction of the entry point and the clear section being located at the fold; and cutting the thread ends and closing the incision at the entry point.

20. The method claimed in claim 19, including threading the ends of the surgical thread by threading needles attached one to each end of the surgical thread through the entry point and one through each exit point.

21. The method claimed in claim 20, including cutting the thread ends flush with the tissue.

22. The method claimed in claim 20, including cutting the needles off the thread ends and knotting the thread ends subcutaneously.

23. The method claimed in claim 20, including threading one of the needles back into its corresponding exit point and subcutaneously towards and out of the other exit point such that both thread ends exit from the same exit point.

24. The method claimed in claim 23, including cutting the needles off the thread ends and tying the thread ends into a knot subcutaneously.

25. The method claimed in claim 19, including selecting exit points on the scalp behind the hairline.

26. The method claimed in claim 19, including locating the entry point above the brow for a brow lift.

27. The method claimed in claim 19, including locating the entry point on the mid point of the malar mound for a mid face suspension.

28. The method claimed in claim 27, including making a second entry point for a second lift on the bottom of the malar mound for a fuller mid face suspension.

29. The method claimed in claim 19, including locating an entry point anterior to the hair line and the exit points high in the temporal scalp for an intra hairline suspension.

30. The method claimed in claim 19, including locating the entry point just below the lateral canthus for a lateral canthal suspension.

31. The method claimed in claim 19, including locating the entry point at the level of the angle of mandible through the bulk of the jowl mound for a jowl suspension.

32. The method claimed in claim 19, including locating two separate entry points for two separate lifts in two of the platysmal bands for a neck lift.

33. The method claimed in claim 19, including providing the clear section with a better hold against the tissue whereby the clear section is made flat.

34. The method claimed in claim 19, including providing a better hold of the clear section against the tissue, whereby the clear section is provided with a sleeve having a roughened surface.

35. The method claimed in claim 19, including providing a better hold of the clear section against the tissue, whereby the clear section is braided with more than one thread.

36. The method claimed in claim 19, including threading the ends of the surgical thread through a cannula that is first passed through the entry point and first the exit point.

37. A method of performing plastic surgery operations using a surgical thread having a clear section and multiple sharp projections on either side of the clear section, wherein the clear section is devoid of projections and is approximately 4 cm in length to create a holding zone when the surgical thread is folded at the clear section, and the projections on both sides of the clear section are inclined toward the clear section, the method including:

making an incision into tissue at an entry point defining the point of tissue lift;

threading one end of the surgical thread from the entry point subcutaneously through tissue and/or muscle and out of a first exit point from where tissue is to be suspended, whereby the thread is threaded until the clear section nears or enters the incision;

threading the other end of the surgical thread through the entry point and subcutaneously through tissue and/or muscle and out of a second exit point spaced from a first exit point thereby folding the thread back on itself to foiin a loop or sling;

adjusting the thread tension from both ends of the thread to achieve a desired lift along a direction from the point of tissue lift toward the first and second exit points, the projections resisting thread pull in the direction of the entry point and the clear section being located at the fold; and cutting the thread ends and closing the incision at the entry point.

38. The method claimed in claim 37, including threading the ends of the surgical thread by threading a needle attached to at least one end of the surgical thread through at least one of the entry point, the first exit point, and the second exit point.

39. The method claimed in claim 37, including threading the ends of the surgical thread by threading a cannula attached to at least one end of the surgical thread through at least one of the entry point, the first exit point, and the second exit point.

40. A surgical thread for plastic surgery operations comprising a clear section and multiple sharp projections on either side of the clear section, wherein the clear section is devoid of projections and is approximately 4 cm in length to create a holding zone when the surgical thread is folded to form a loop or a sling at the clear section, and the projections on both sides of the clear section are inclined toward the clear section, wherein sharp projections occupy a length of about 20 cm on either side of the clear section, wherein the thread has end zones at the end of the thread that are clear of sharp projections, wherein the end zones are approximately 8 to 10.5 cm in length.

41. The surgical thread claimed in claim 40, wherein at least one end zone is attached to a needle.

* * * * *